US011209415B2

(12) United States Patent
Wang et al.

(10) Patent No.: US 11,209,415 B2
(45) Date of Patent: Dec. 28, 2021

(54) DISCRETE ELEMENT METHOD FOR MODELLING A FRACTURE EVOLUTION OF A ROADWAY SURROUNDING ROCK

(71) Applicants: China University of Mining and Technology, Jiangsu (CN); China Mining & Civil New Material Science and Technology Ltd., Jiangsu (CN); BOXIA MINING TECHNOLOGY LTD., Jiangsu (CN)

(72) Inventors: Xiangyu Wang, Jiangsu (CN); Jianbiao Bai, Jiangsu (CN); Junwu Xia, Jiangsu (CN); Shuai Yan, Jiangsu (CN)

(73) Assignees: China University of Mining and Technology, Jiangsu (CN); China Mining & Civil New Material Science and Technology Ltd., Jiangsu (CN); BOXIA MINING TECHNOLOGY LTD., Jiangsu (CN)

( * ) Notice: Subject to any disclaimer, the term of this patent is extended or adjusted under 35 U.S.C. 154(b) by 0 days.

(21) Appl. No.: 17/043,707

(22) PCT Filed: Oct. 8, 2019

(86) PCT No.: PCT/CN2019/109932
§ 371 (c)(1),
(2) Date: Sep. 30, 2020

(87) PCT Pub. No.: WO2021/007959
PCT Pub. Date: Jan. 21, 2021

(65) Prior Publication Data
US 2021/0263003 A1    Aug. 26, 2021

(30) Foreign Application Priority Data
Jul. 15, 2019    (CN) .......................... 201910635883.6

(51) Int. Cl.
*G01N 33/24*    (2006.01)
*G06F 30/25*    (2020.01)
(Continued)

(52) U.S. Cl.
CPC ............... *G01N 33/24* (2013.01); *G01N 3/08* (2013.01); *G06F 30/25* (2020.01);
(Continued)

(58) Field of Classification Search
CPC .. G01N 33/24; G01N 2203/0019; G01N 3/08; G06F 30/25; G06F 30/20; G06F 30/23; G06F 2111/10
See application file for complete search history.

(56) References Cited

U.S. PATENT DOCUMENTS 11,098,582 B1 *    8/2021    Camargo ................. E21B 43/26
2013/0238304 A1 *    9/2013    Glinsky ............... G01V 99/005
703/6

FOREIGN PATENT DOCUMENTS

| CN | 106919770 | 7/2017 |
| CN | 109271738 | 1/2019 |
| CN | 109492262 | 3/2019 |

OTHER PUBLICATIONS

"International Search Report (Form PCT/ISA/210) of PCT/CN2019/109932," dated Nov. 28, 2019, pp. 1-3.

* cited by examiner

*Primary Examiner* — Jonathan M Dunlap
(74) *Attorney, Agent, or Firm* — JCIPRNET (57) ABSTRACT

A discrete element method for modelling fracture evolution of roadway surrounding rock is provided, which includes: taking rock cores from a coal seam in the field and recording RQD values, observing roadway deformation, and making a statistical analysis on distribution characteristics of fractures in the coal seam; testing mechanical parameters of coal-rock (Continued)

samples indoors, and calculating strength of a rock mass according to the RQD values; creating a numerical model by using a UDEC-Trigon module to adjust the parameters to match the strength of the rock mass, and correcting model parameters; and creating a numerical model of an engineering scale to adjust the parameters to match field deformation characteristics, and finally simulating fracture evolution of the roadway surrounding rock. The present invention provides accurate and basic mechanical parameters for discrete-element numerical simulation of roadway deformation, guaranteeing realistic and reliable simulation results.

7 Claims, 12 Drawing Sheets

(51) Int. Cl.
    *G01N 3/08*         (2006.01)
    *G06F 30/23*       (2020.01)
    *G06F 30/20*       (2020.01)
    *G06F 111/10*     (2020.01)

(52) U.S. Cl.
    CPC ...... *G01N 2203/0019* (2013.01); *G06F 30/20* (2020.01); *G06F 30/23* (2020.01); *G06F 2111/10* (2020.01)

DISCRETE ELEMENT METHOD FOR MODELLING A FRACTURE EVOLUTION OF A ROADWAY SURROUNDING ROCK

CROSS-REFERENCE TO RELATED APPLICATION

This application is a 371 of international application of PCT application serial no. PCT/CN2019/109932, filed on Oct. 8, 2019, which claims the priority benefit of China application no. 201910635883.6, filed on Jul. 15, 2019. The entirety of each of the above mentioned patent applications is hereby incorporated by reference herein and made a part of this specification.

FIELD OF THE INVENTION

The present invention relates to the field of coal mining technologies, and in particular, to a discrete element method for simulating fracture evolution of roadway surrounding rock.

DESCRIPTION OF RELATED ART

Stability of a coal pillar is always the focus of research on safe and efficient mining. As mining depth increases and geological conditions become complicated, large deformations may occur during gob-side entry driving and gas may leak out from a mined-out area, causing poor control on roadway surrounding rock. An improper reserved width of the coal pillar and unclear understanding of failure mechanisms of the coal pillar and the surrounding rock result in a failure to propose a control measure effective for a long time, severely affecting safe and efficient mining of coal resources.

A numerical simulation method has obvious advantages in solving engineering problems, and mainly includes a finite element method and a discrete element method. A discrete-element numerical model can simulate a failure process of a rock mass and explicitly simulate fracture extension and evolution, thus being widely applied in solving underground geotechnical problems. A UDEC (Universal Distinct Element Code) Trigon model, which is a non-continuous model further improved from the Voronoi polygon, is formed by blocks and a joint. Damage to the joint between the blocks is triggered under different stress, and initial fractures and newly produced fractures can be clearly differentiated from one another, so that a fracture evolution process of the roadway surrounding rock can be realistically simulated.

The existing numerical simulation method and technique have the following shortcomings in simulation of roadway deformation: Mechanical parameters measured in the laboratory are directly selected as rock-mass mechanical parameters for the model and are applied in the numerical model. However, samples used in the laboratory are generally small. Formed after exploitation and cutting of rockmass, the samples are changed in internal stress and structure in this process, and thus have great difference from a rockmass. The existing numerical simulation method and technique overlook the difference between a rockmass and a intact rock, attaining a final result greatly deviating from an actual field situation. Therefore, the existing method and technique cannot be depended on to direct field operations.

SUMMARY OF THE INVENTION

The objective of the present invention is to provide a discrete element method for modelling fracture evolution of roadway surrounding rock, which can effectively and realistically reproduce field situations, and obtain realistic and reliable simulation results.

To achieve the foregoing objective, the present invention adopts a discrete element method for simulating fracture evolution of roadway surrounding rock, including the following steps:

S1: in a test roadway, observing deformation characteristics of the roadway and taking rock cores from coal seam and rockmass; recording deformation characteristics of the roadway surrounding rock, and monitoring distribution characteristics of fractures in roof and two ribs of the roadway; and taking rock cores from the roof and a coal seam, and recording RQD values of the roof rock cores and the coal seam rock cores;

S2: separately making the obtained roof rock cores and coal seam rock cores into standard intact rock, and carrying out experiments in mechanics to test uniaxial compressive strength, Brazilian tensile strength, and an elastic modulus of the intact rocks; and according to a functional relationship between a ratio of the elastic modulus of a rock mass to that of the intact rock and the RQD, and a functional relationship between the uniaxial compressive strength of the rock mass and that of the intact rock, determining uniaxial compressive strength and an elastic modulus of the rock mass, where Brazilian tensile strength of the rock mass is 0.1 of its uniaxial compressive strength;

S3: creating a calibration model by using a Trigon logic in the UDEC, where an average value of side lengths of triangular blocks in the model is determined according to the fracture distribution characteristics statistically analyzed in step S1; by using the uniaxial compressive strength, Brazilian tensile strength, and elastic modulus of the rock mass calculated in step S2 as known characteristic values, performing an inversion with the calibration model to obtain triangular block parameters and joint parameters in the correction model;

S4: creating a numerical model with a mining scale of a field working face by using the UDEC, defining an area of study, and dividing the area of study into triangular blocks by using the Trigon model, where an average value of edge lengths of the triangular blocks and the triangular block parameters are identical with those in the calibration model in step S3; forming rectangular blocks increasingly growing in length by division in areas outside the area of study; and based on the deformation characteristics of the roadway surrounding rock and the fracture distribution characteristics that are observed in step S1, performing an inversion to obtain mechanical parameters of the rectangular blocks in the field-scale model.

According to some embodiments of the present invention, the triangular block parameters and the joint parameters in the calibration model that are obtained by inversion in step S3 respectively include a size and an elastic modulus of the triangular block, and normal stiffness, shear stiffness, cohesion, friction angle, and tensile strength of the joint; and an inversion method specifically includes:

a) separately creating a rectangular calibration model of 2 m in width and 4 m in height and a circular calibration model with a diameter of 2 m, where an average value of the side lengths of the triangular blocks is guaranteed to be consistent with a fracture length obtained based on field statistics;

b) setting the elastic modulus of the triangular blocks in the model to be equal to that of the rock mass calculated according to a formula (II);

c) deducing normal stiffness $K_n$ of the joint between the triangular blocks according to a formula (IV), a ratio of the shear stiffness $K_s$ to $K_n$ being 0.2; and determining the Poisson's ratio µ according to a variation in $K_s/K_n$, where the formula (IV) is specifically as follows:

$$K_n = n\left[\frac{K+(4/3)G}{\Delta Z_{min}}\right](1 \leq n \leq 10) \quad (IV)$$

where K and G are respectively a volume modulus and a shear modulus of the triangular blocks, in GPa, and are calculated according to equations K=E/3(1−2µ) and G=E/2(1+µ), µ being the Poisson's ratio of the block, and E being an elastic modulus of the block, in GPa; $\Delta Z_{min}$ is a minimum width of adjoining units in a vertical direction, in m; and n is equal to 10; and d) carrying out a uniaxial compression test and Brazilian splitting test for many times by using the calibration model, to obtain stress-strain curves; employing the means of trial and error iteration to make simulated mechanical parameters match the uniaxial compressive strength, Brazilian tensile strength, and elastic modulus of the rock mass calculated in step S2; and finally performing an inversion to obtain cohesion, friction angle, and tensile strength of the joint in the model.

According to some embodiments of the present invention, in step S1, a roadway surface displacement measuring station is mounted by means of a crisscross layout, the deformation characteristics of the roadway surrounding rock are recorded with an explosion-proof camera, the distribution characteristics of fractures in the roof and two walls of the roadway are monitored with a drilling observation instrument, and a distribution characteristics of lengths of fractures in the surface of a drill hole is quantified by means of drilling tracing.

According to some embodiments of the present invention, in step S1, the RQD represents rock quality designation which is expressed by the following specific equation:

$$RQD = \frac{l}{L} \times 100\% \quad (I)$$

where l is a cumulative length of rock cores greater than or equal to 10 cm in length, in m; and L is a total length of the drill hole.

According to some embodiments of the present invention, in step S2, the functional relationship between a ratio of the elastic modulus of the rock mass to that of the rock block and the RQD is expressed by the following specific equation:

$$E_m/E_r = 10^{0.0186RQD-1.91} \quad (II)$$

where $E_m$ is the elastic modulus of the rock mass, in GPa; and $E_r$ is the elastic modulus of the intact rock, in GPa.

According to some embodiments of the present invention, in step S2, the functional relationship between the uniaxial compressive strength of the rock mass and that of the intact rock is expressed by the following specific equation:

$$\left(\frac{\sigma_{cm}}{\sigma_c}\right) = \left(\frac{E_m}{E_r}\right)^m \quad (III)$$

where $\sigma_{cm}$ and $\sigma_c$ and are the uniaxial compressive strength of the rock mass and that of the intact rock respectively, in MPa; and m is equal to 0.63.

The present invention has the following advantageous technical effects: In consideration of differences between an rock mass and intact rock, mechanical parameters of the rock mass are calculated according to a functional relationship between a rock quality designation RQD and a ratio of an elastic modulus of the rock mass to that of the intact rock, and according to a functional relationship between uniaxial compressive strength of the rock mass and that of the intact rock, a calibration model is created by using a Trigon logic in UDEC, and an inversion is performed to obtain rock-mass parameters for a numerical calculation model, so that roadway deformation characteristics in the field can be simulated realistically and reliably. Therefore, the parameter correction method for discrete-element simulation of roadway deformation proposed in the present invention overcomes the existing problem that it is difficult to determine parameters for numerical simulation, and can realistically reproduce field situations, so that the simulation results are realistic and reliable. Thus, the present invention guarantees safe and efficient mining to a certain extent, and can be used to guide field operations.

DETAILED DESCRIPTION OF THE INVENTION

The present invention is further described in detail below with reference to the accompanying drawings and a specific embodiment. It should be noted that the following embodiments are merely used for description of the present invention, and are not intended to limit the present invention.

Figure 1:
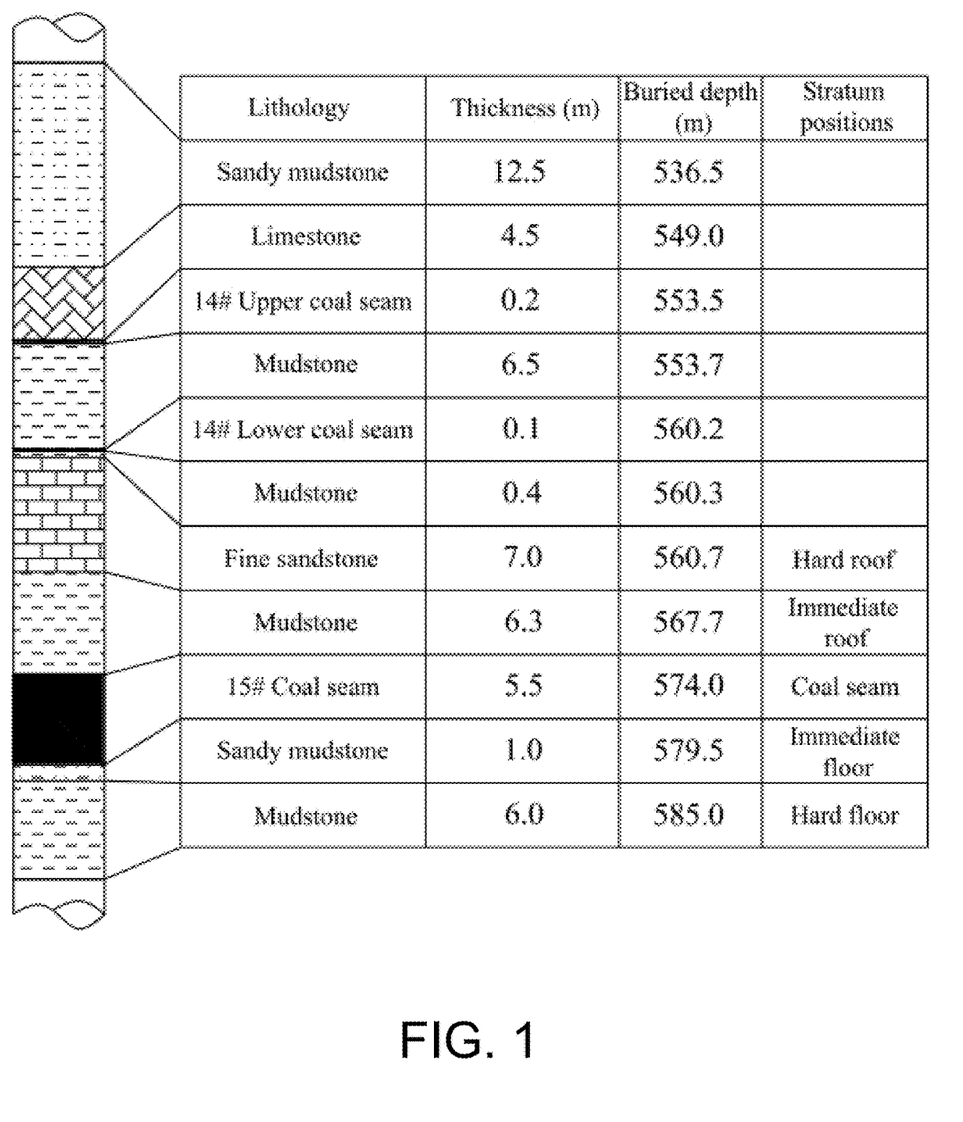
FIG. 1 shows a generalized stratigraphic column of the test site.
Figure 2A:
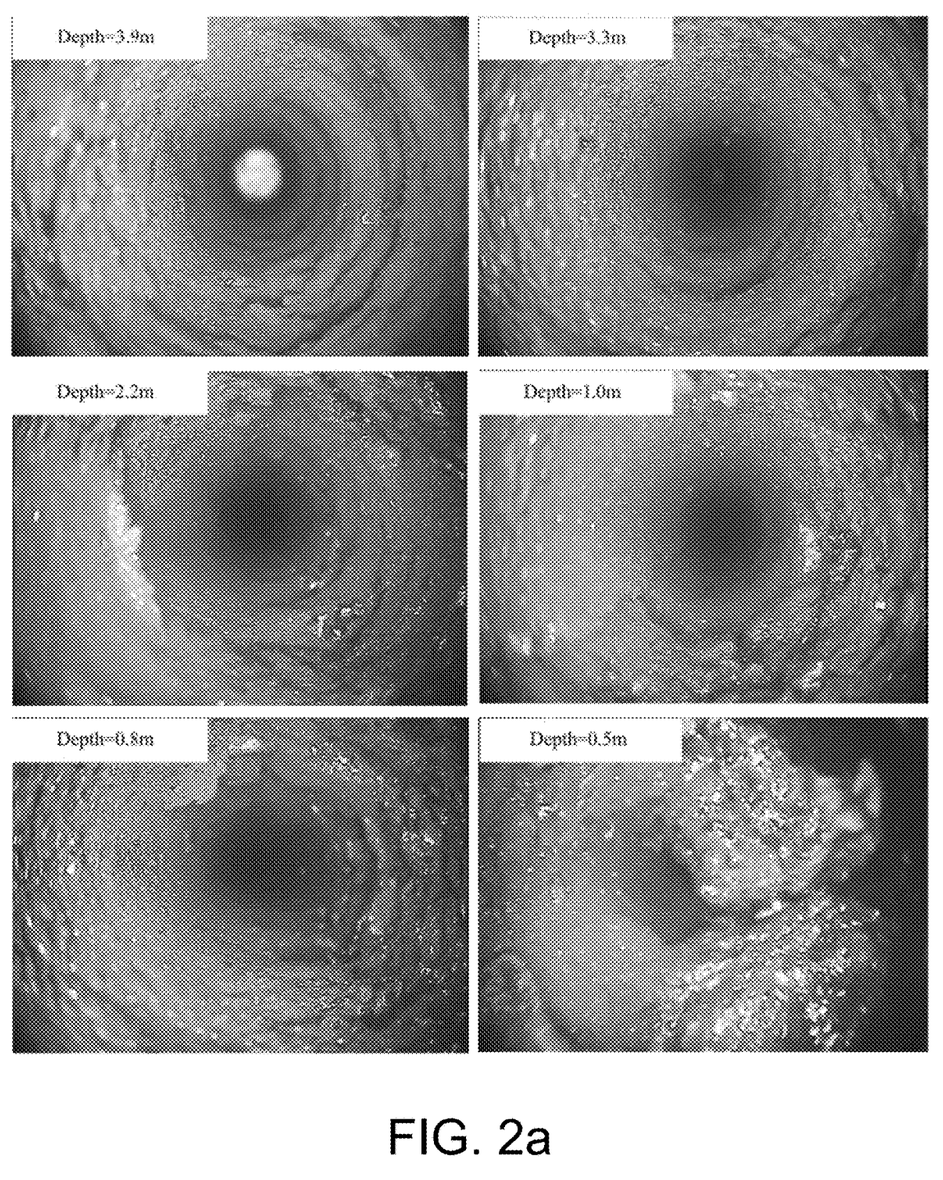
FIG. 2a shows fracture distribution characteristics on a coal pillar rib.
Figure 2B:
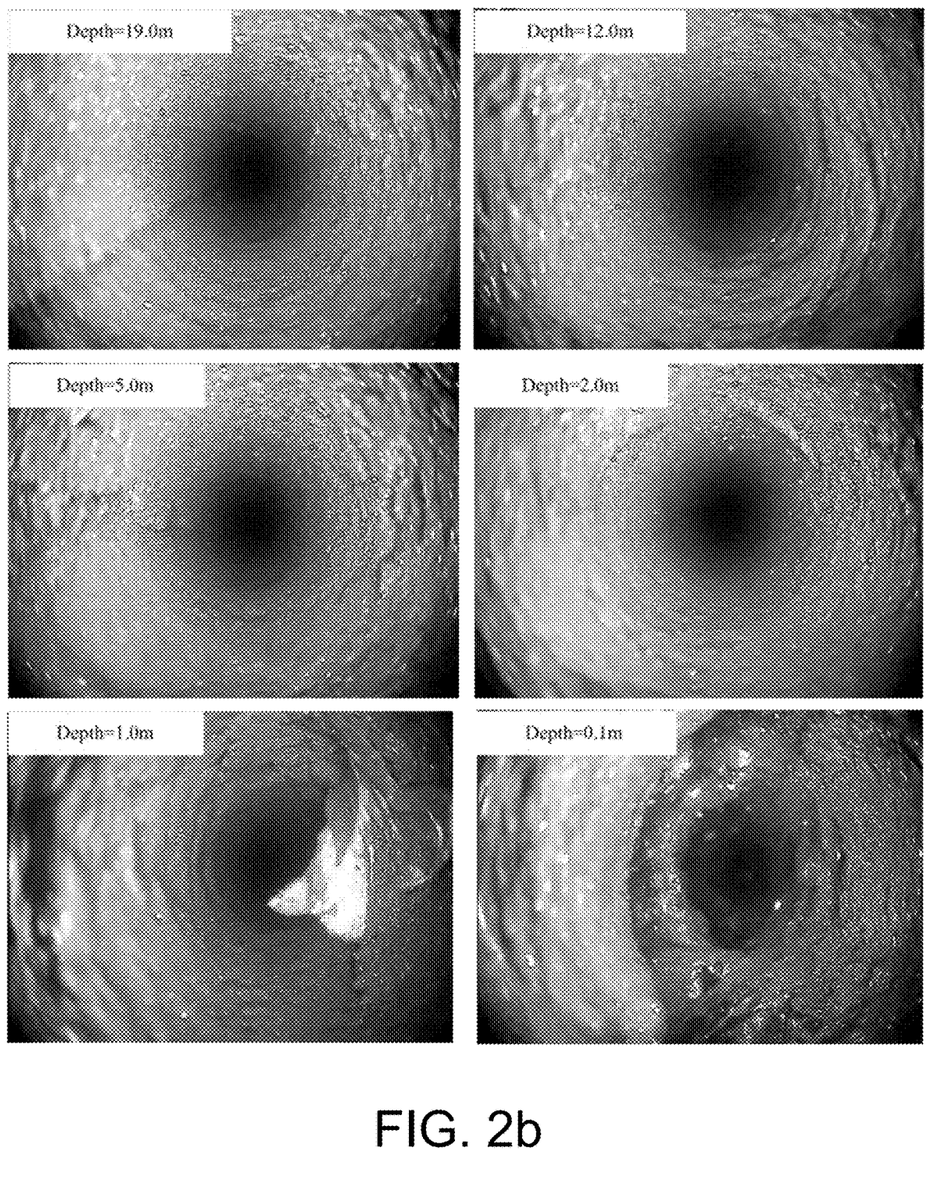
FIG. 2b shows fracture distribution characteristics on a virgin coal rib.

The embodiment takes gob-side entry driving in a narrow coal pillar of 7 m in width in the 15106 tailgate in Sijiazhuang Mine of Yangquan Coal Group as an engineering background. Coal seam in this case have an average buried depth of 574 m and an average thickness of 5.5 m, and joint fractures develop therein. The 15106 tailgate has an overall length of 1700 m. Roadway excavation is conducted along the roof of the coal seam, and an excavation section is a rectangle of 4.8 m in width×4.0 m in height. A drill hole columnar section of the coal seam is shown in FIG. 1. Herein, a method of the present invention is used to correct parameters in a numerical model for modelling simulating roadway deformation. A discrete element method for simulating fracture evolution of roadway surrounding rock in this embodiment includes the following several steps:

1) Samples are taken from a complete roof and floor in the 15106 tailgate, and RQD values corresponding to different lithology are recorded. A YTJ20-model drilling observation instrument developed and manufactured by China University of Mining and Technology is used to explore a narrow coal pillar rib and a solid coal rib. A horizontal exploration hole is made at a distance of 2 m to the floor, with a diameter of 29 mm. A drill hole at a depth of 4 m is made in the coal pillar side, and a drill hole at a depth of 20 m is made in the solid coal side. Distribution characteristics of fractures on the two ribs obtained by observation are shown in FIG. 2a and FIG. 2b respectively. It can be learned from FIG. 2a and FIG. 2b that, on the coal pillar side, a lot of annular through fractures and vertical fractures are produced within an observed range of 4 m. Coal close to a wall portion of the coal pillar is already damaged, to form a broken zone and cause hole collapse. A mined-out area is on the other side of the coal pillar, and cannot be observed with the drilling observation instrument. However, it may be inferred according to the drilling observation result that the degree of damage of the coal pillar adjacent to the gob side is likely to be similar to or more serious than that in the roadway. Therefore, it can be determined that in the 15106 tailgate, fractures develop inside the coal pillar after roadway excavation, and the whole coal pillar is already yield. On the solid coal side, a coal seam within a distance of 1 m to the coal wall is seriously broken; a few fractures exist within a range of 1 m to 2 m; and a coal seam deeper than 2 m is unaffected by mining and almost complete, without relatively large fractures.

Figure 3A:
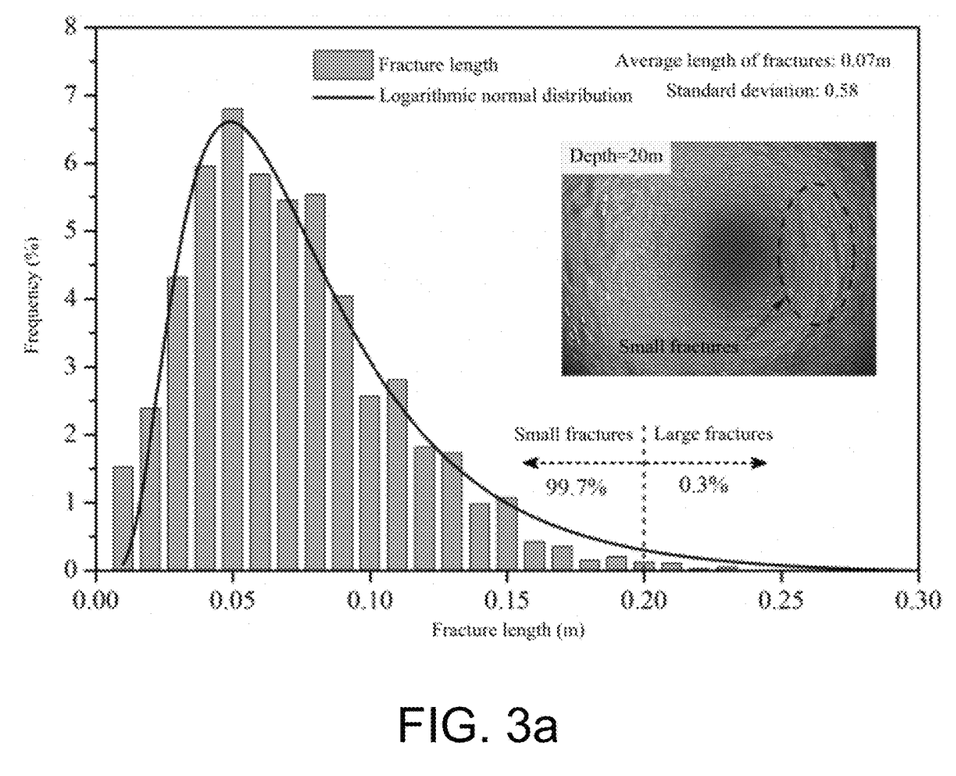
FIG. 3a is a probability distribution of fractures' length in the coal pillar.
Figure 3B:
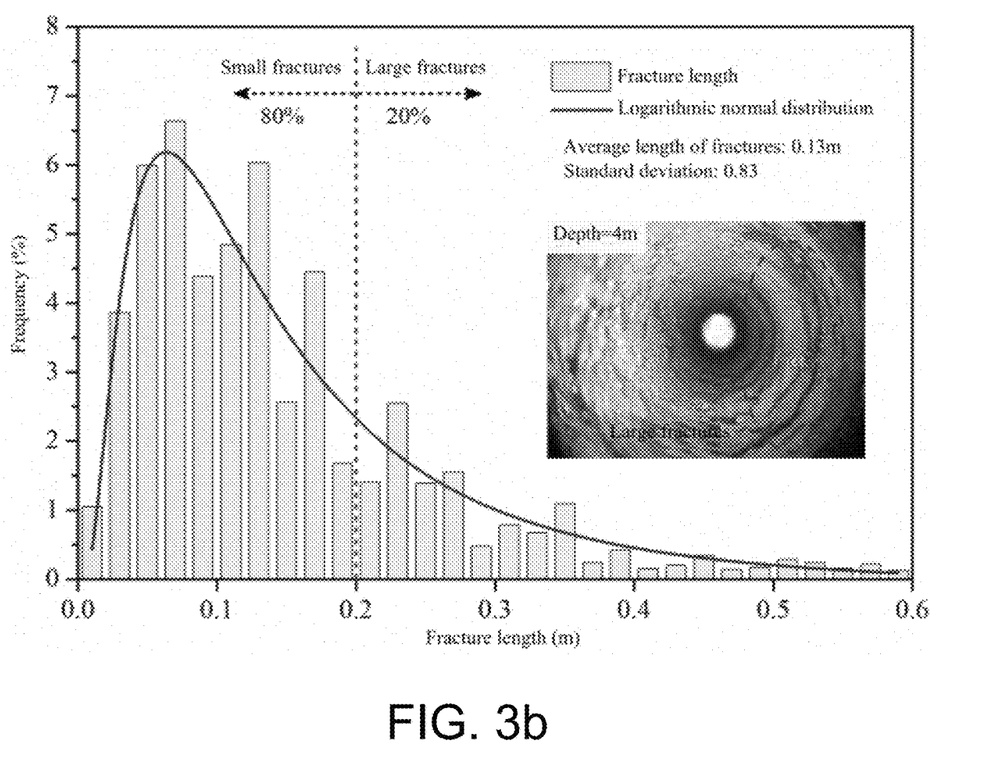
FIG. 3b is a probability distribution of fractures' length in the virgin coal seam.

By means of drilling tracing, a statistical analysis on lengths of the fractures in the coal pillar and the solid coal is made, to obtain results shown in FIG. 3a and FIG. 3b respectively. It can be learned from FIG. 3a and FIG. 3b that the lengths of the fractures in the coal pillar and the solid coal meet a logarithmic normal distribution rule. The lengths of the fractures in the solid coal range from 0.01 m to 0.23 m and have an average value of 0.07 m, where fractures less than 0.2 m in length account for 99.7% of the total, and there are almost no large fractures (greater than 0.2 m in length). The lengths of the fractures in the coal pillar range from 0.03 m to 0.59 m and have an average value of 0.13 m, where fractures less than 0.2 m in length account for 80% of the total, and large fractures account for 20% of the total. It can be learned by comparison between FIGS. 3a and 3b that, no large fractures exist in the solid coal unaffected by mining, and the 20% large fractures in the coal pillar are not original fractures in natural coal but produced due to damage during formation of the coal pillar. These large fractures are unable to represent the natural initial fractures. Therefore, the initial fractures in the coal seam are required to be less than 0.2 m in length, to provide basic data for establishment of a calibration model.

2) Rock cores obtained in step 1) are made into standard samples which are cylinders with a diameter of 50 mm and a height of 100 mm and small cylinders with a diameter of 50 mm and a thickness of 25 mm, and then a uniaxial compression test and a Brazilian splitting test are performed on these cylinders, to test uniaxial compressive strength, tensile strength, and an elastic modulus of the rock samples. Strength and an elastic modulus of a rock mass are calculated according to formulae (II) and (III), where tensile strength of the rock mass is 0.1 of its uniaxial compressive strength. Test results are shown in table 1.

TABLE 1

Properties of intact rock and calculated rock mass in the Sijiazhuang coal mine

| Rock strata | Intact rock | | | Rock mass | | |
|---|---|---|---|---|---|---|
| | Elastic modulus $E_r$/GPa | Uniaxial compressive strength $\sigma_c$/MPa | RQD | Elastic modulus $E_m$/GPa | Uniaxial compressive strength $\sigma_{cm}$/MPa | Tensile strength $\sigma_{tm}$/MPa |
| Fine sandstone | 23.4 | 48.9 | 92 | 14.8 | 36.6 | 3.66 |
| Mudstone | 10.6 | 16.6 | 76 | 3.4 | 8.1 | 0.81 |
| Coal seam | 3.2 | 10.5 | 72 | 0.86 | 4.6 | 0.46 |
| Sandy mudstone | 14.2 | 21.0 | 85 | 6.6 | 13.0 | 1.30 |

The test results suggest that the rock mass and the small-scale intact rock have a clear difference in mechanical parameters, where the elastic modulus and the uniaxial compressive strength are both reduced to varying degrees. The results further suggest that it is improper to directly put mechanical parameters of a small stone measured in the laboratory into a numerical model for calculation, and further correction is required to match the parameters of the rock mass.

A functional relationship between a ratio of the elastic modulus of the rock mass to that of the rock block and the RQD is expressed by the following specific equation:

$$E_m/E_r = 10^{0.0186RQD-1.91} \quad (II)$$

In the equation, $E_m$ is the elastic modulus of the rock mass, in GPa; and $E_r$ is the elastic modulus of the intact rock, in GPa.

A functional relationship between the uniaxial compressive strength of the rock mass and that of the intact rock is expressed by the following specific equation:

$$\left(\frac{\sigma_{cm}}{\sigma_c}\right) = \left(\frac{E_m}{E_r}\right)^m \quad (III)$$

In the equation, $\sigma_{cm}$ and $\sigma_c$ and a are respectively the uniaxial compressive strength of the rock mass and that of the intact rock, in MPa, where m is equal to 0.63.

Figure 4A:
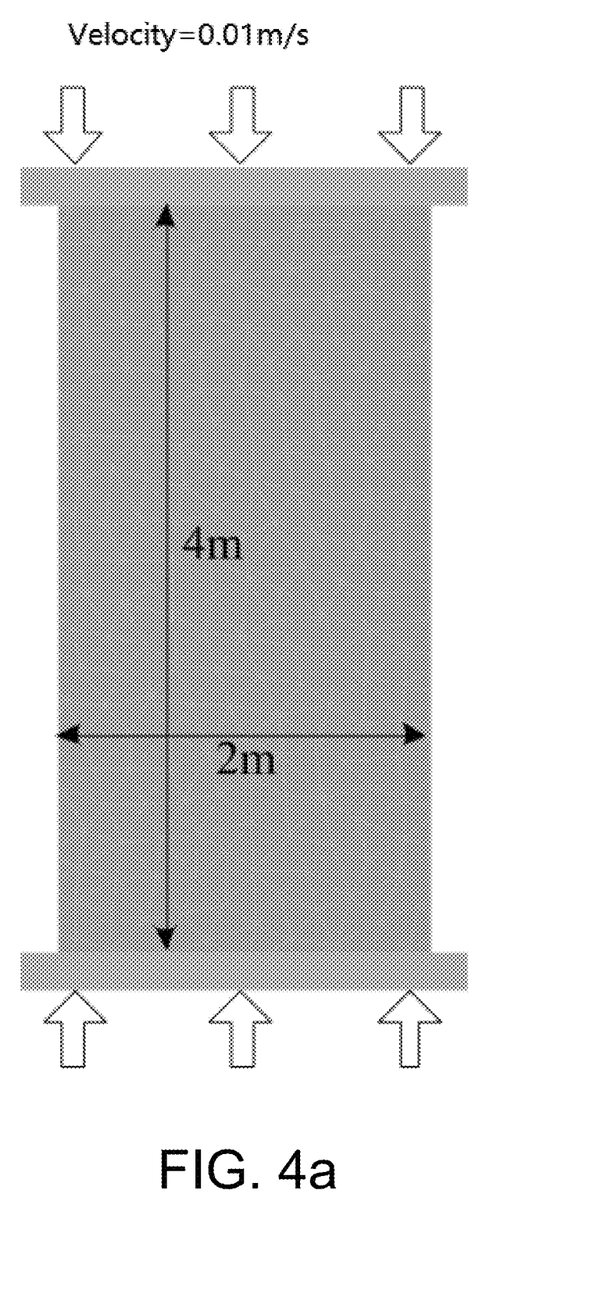
FIG. 4a shows a calibration model for uniaxial compressive strength test.
Figure 4B:
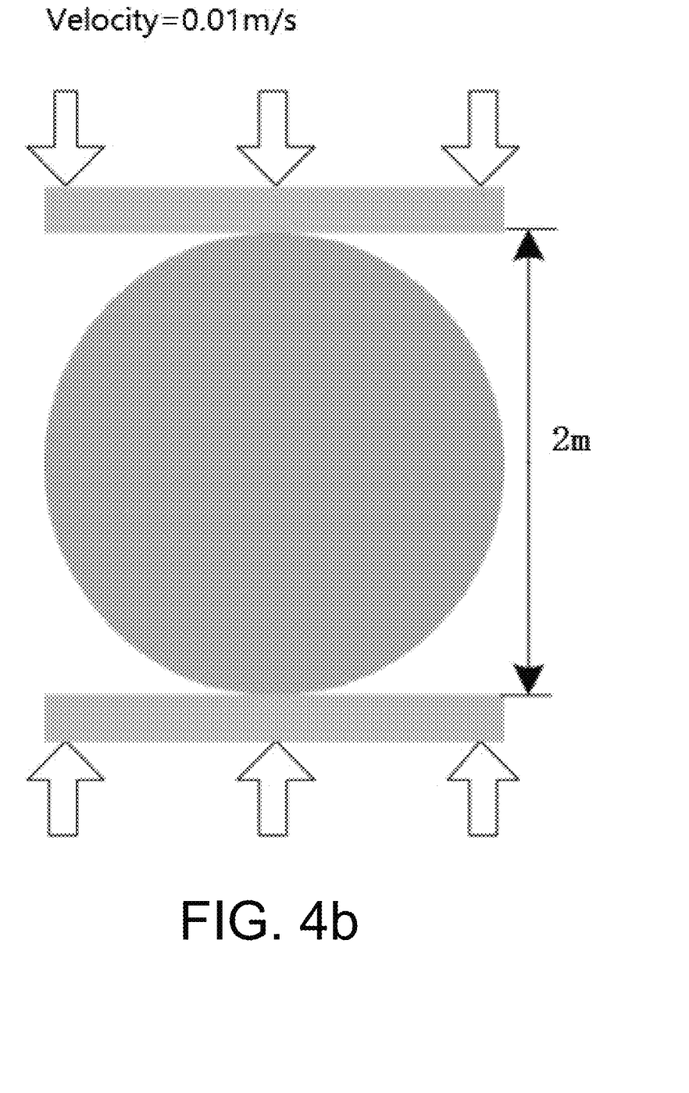
FIG. 4b shows a calibration model for Brazilian tensile strength test.

3) As shown in FIG. 4a, a small-size rectangular correction model of 2 m in width and 4 m in height is created by using a Trigon module in the UDEC, and is used for a uniaxial compression test. As shown in FIG. 4b, a circular correction model with a diameter of 2 m is created for a Brazilian splitting test. Triangles in the model have an average side length of 0.2 m, which is able to represent the size of initial fractures in the coal seam before disturbance, thus easily differentiating newly produced fractures from the initial fractures.

Models are created for correction respectively for the four rock strata with different lithology. Blocks in the models are set to be elastic, that is, the blocks can be deformed but not damaged. A constitutive model based on the Mohr-Coulomb residual strength is used for joints.

The rock mass is damaged only along a joint, and macro-fractures are gradually formed after generation, expansion and penetration of micro-fractures.

The density of the block is identical with an actual density of the rock mass, and is measured in the laboratory. An elastic modulus of the block is identical with the calculated elastic modulus of the rock mass. Stiffness of the joint is determined according to the size of the block unit in the model and a ratio of $K_s/K_n$. An inversion is performed by means of trial and error iteration to obtain cohesion, an friction angle, and tensile strength of the joint of the model.

Figure 5A:
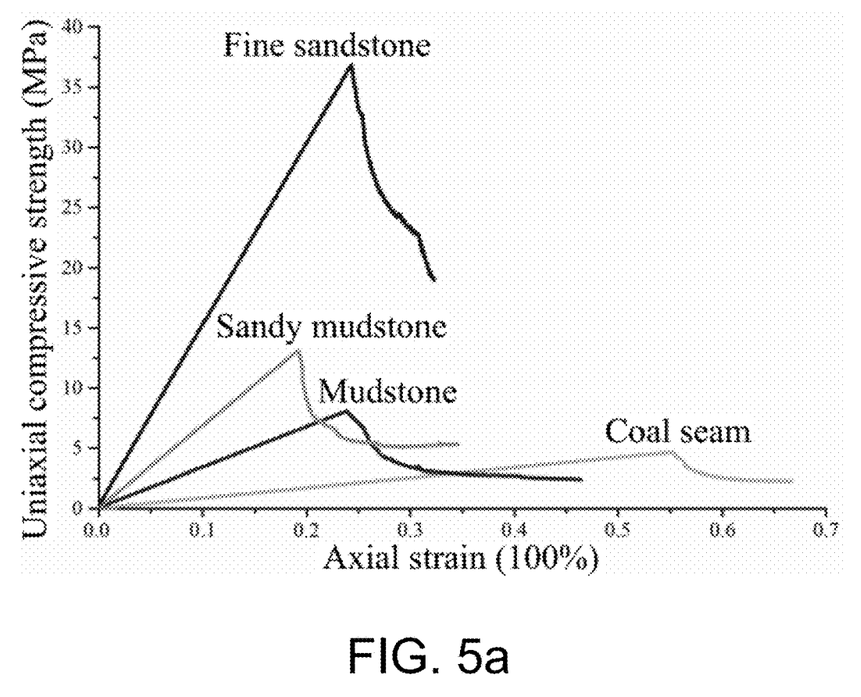
FIG. 5a shows a stress-strain curve regarding uniaxial compression by the calibration model.
Figure 5B:
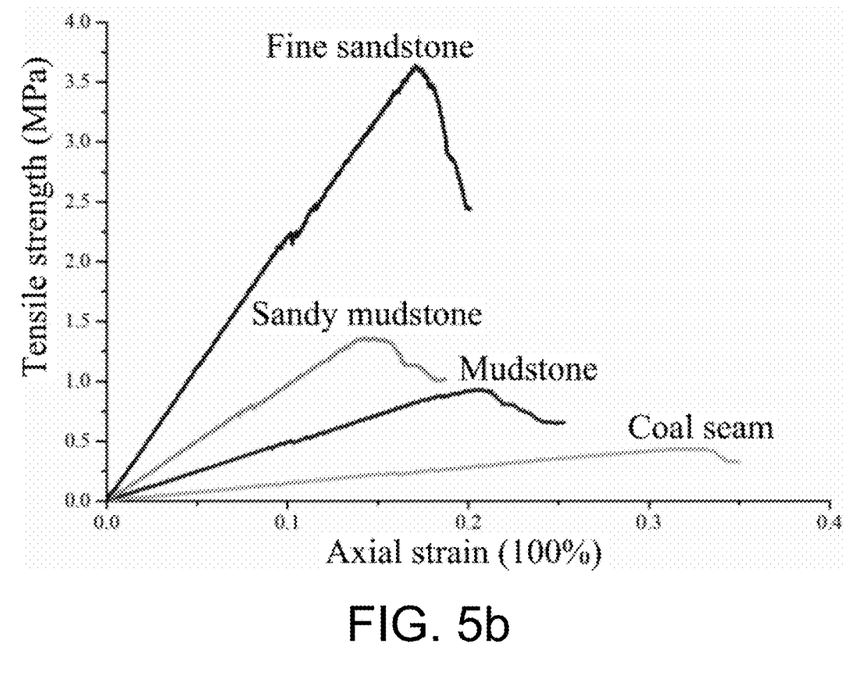
FIG. 5b shows a stress-strain curve regarding Brazilian splitting by the calibration model.

A series of uniaxial compression and Brazilian splitting tests are carried out by using the correction models, to obtain whole-process stress-strain curves, as shown in FIGS. 5a and 5b.

Simulation results match the calculated rock-mass mechanical parameters (the uniaxial compressive strength, tensile strength, and elastic modulus), and finally an inversion is performed to obtain mechanical parameters used for the model, as shown in table 2. According to a joint residual strength criterion, the cohesion and the angle of internal friction of the joint are both reduced to 0 after damage, only retaining a certain residual angle of internal friction.

TABLE 2

Calibrated micro-properties in the Trigon model for field scale model

| | Block parameters | | | Joint parameters | | | | |
|---|---|---|---|---|---|---|---|---|
| Rock strata | Density $Kg/m^3$ | Elastic modulus GPa | Poisson's ratio | Normal stiffness GPa/m | Shear stiffness GPa/m | Cohesion MPa | friction angle (°) (Peak/Residual) | Tensile strength (MPa) |
| Fine sandstone | 2600 | 14.8 | 0.28 | 757 | 151 | 11.7 | 40/33 | 5.55 |
| Mudstone | 2100 | 3.4 | 0.26 | 166.4 | 33.3 | 2.7 | 36/30 | 1.23 |
| Coal seam | 1300 | 0.86 | 0.25 | 160 | 32 | 1.5 | 35/30 | 0.41 |
| Sandy mudstone | 2350 | 6.6 | 0.28 | 337 | 67.5 | 4.2 | 38/32 | 1.97 |

Calibrated results of the mechanical parameters are shown in table 3. As seen from table 3, errors between the corrected mechanical parameters and target values are all less than 10%, which proves that such a parameter correction method is reliable.

TABLE 3

Calibrated results of rock mass properties in the Trigon model

| | Elastic modulus (GPa) | | | Uniaxial compressive strength (MPa) | | | Tensile strength (MPa) | | |
|---|---|---|---|---|---|---|---|---|---|
| Rock strata | Target values | Corrected values | Errors (100%) | Target values | Corrected values | Errors (100%) | Target values | Corrected values | Errors (100%) |
| Fine sandstone | 14.8 | 15.07 | 1.82 | 36.6 | 36.87 | 0.74 | 3.66 | 3.65 | −0.27 |
| Mudstone | 3.4 | 3.37 | −0.88 | 8.1 | 8.12 | 0.25 | 0.81 | 0.89 | 9.88 |
| Coal seam | 0.86 | 0.84 | −2.33 | 4.6 | 4.67 | 1.52 | 0.46 | 0.44 | −4.35 |
| Sandy mudstone | 6.6 | 6.74 | 2.12 | 13.0 | 13.14 | 1.08 | 1.30 | 1.36 | 4.62 |

Figure 6:
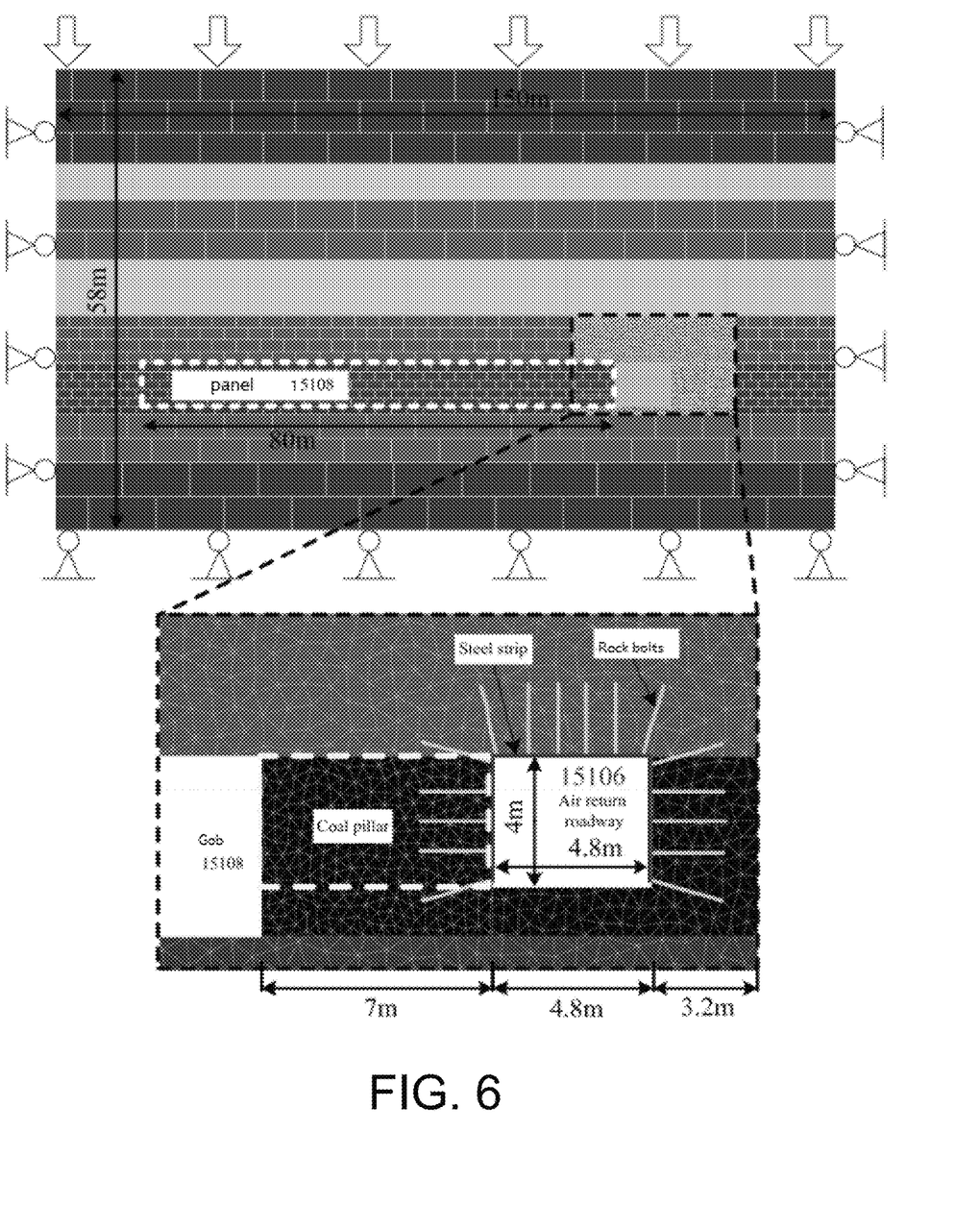
FIG. 6 shows a numerical model of a field scale.

4) According to geological conditions of the panel 15106, a numerical model is created by using UDEC discrete element software, where the model has a length of 150 m and a height of 58 m. In order to improve calculation efficiency, a key area of study is divided into triangular blocks with the Trigon module, as shown in FIG. 6. The triangular blocks in a coal pillar zone have side lengths of 0.2 m, those in a surrounding coal seam zone have side lengths of 0.4 m, and those in zones of the immediate roof and floor of the coal seam have side lengths of 0.5 m. Rectangular blocks increasingly growing in length are formed by division in areas outside the area of study, and have varying lengths of 1.1 m, 2 m and 7 m. Such a block size setting manner can effectively simulate mechanical behavior of the coal pillar.

Left and right boundaries of the model are fixed horizontally, the bottom is fixed vertically, a pressure equivalent to overburden weight is applied to the top, and in-situ stress field measured in site is applied inside the model. Values of parameters for the model are set according to the corrected parameters in table 2. An excavation plan is carried out according to an actual mining order. A working face 15108 is first excavated, and the 15106 tailgate is then excavated after balancing by model calculation. A reserved width of the coal pillar is 7 m. A roadway support manner is simulated according to actual support parameters. Based on the deformation characteristics of the roadway surrounding rock and the fracture distribution rule that are observed in step 1), an inversion is performed to obtain mechanical parameters of the rectangular blocks in the large model.

Figure 7:
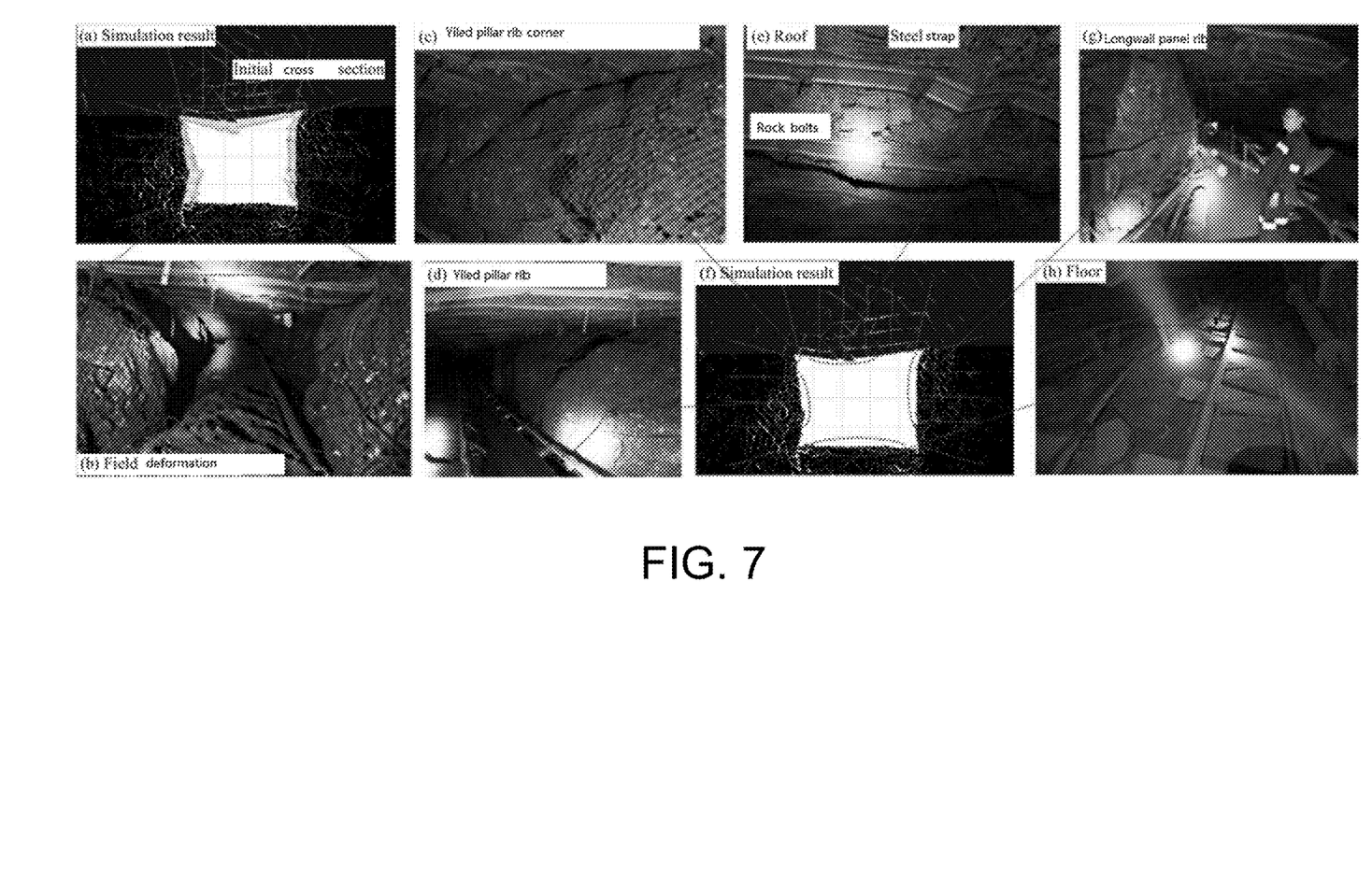
FIG. 7 is a diagram showing a comparison between roadway deformation in numerical simulation and field observations.

FIG. 7 shows a comparison between simulated roadway deformation and a field observation result. It can be learned from FIG. 7 that, the roadway has been seriously damaged during excavation, the roof-to-floor convergence is about 592 mm, and the rib-to-rib convergence is 696 mm. These statuses are consistent with roadway deformation statuses (in which the roof-to-floor convergence is 540 mm, and the rib-to-rib convergence is 645 mm, as shown in (b) of FIG. 7.) observed at a distance of 610 m to a roadway entrance. In (c) to (g) of FIG. 7 show a comparison regarding damage forms between numerical simulation and field observation. A comparison result suggests that, affected by mining stress, the roof of the field roadway subsides, the two walls are squeezed towards the space of the roadway, and the floor heaves, resulting in fracture of a roof steel strip and deformation of rails laid on the floor. The coal pillar has the maximum degree of deformation, which mainly occurs on the lower half part thereof; and firmly presses a coal delivery belt. The foregoing roadway damage forms observed during excavation in the field can all be realistically captured in the UDEC Trigon model, as shown in (f) of FIG. 7.

Figure 8:
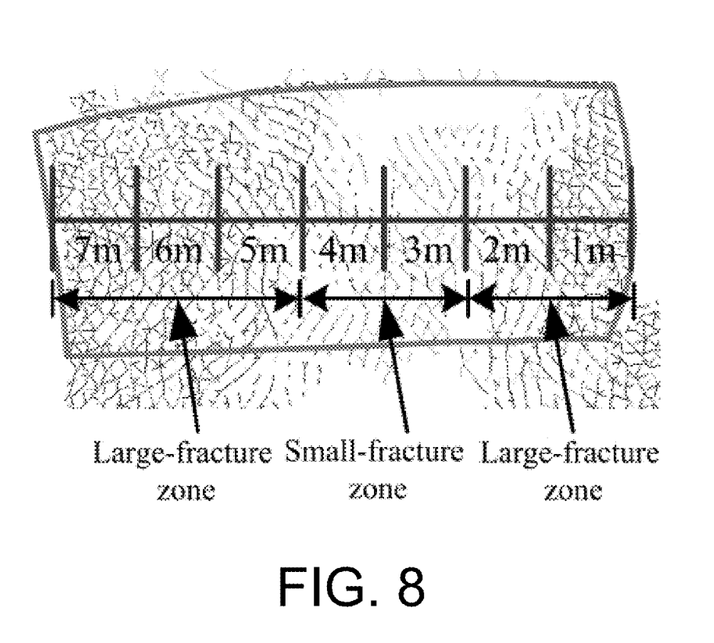
FIG. 8 shows distribution of fractures in a coal pillar of 7 m in width after simulation.
Figure 9:
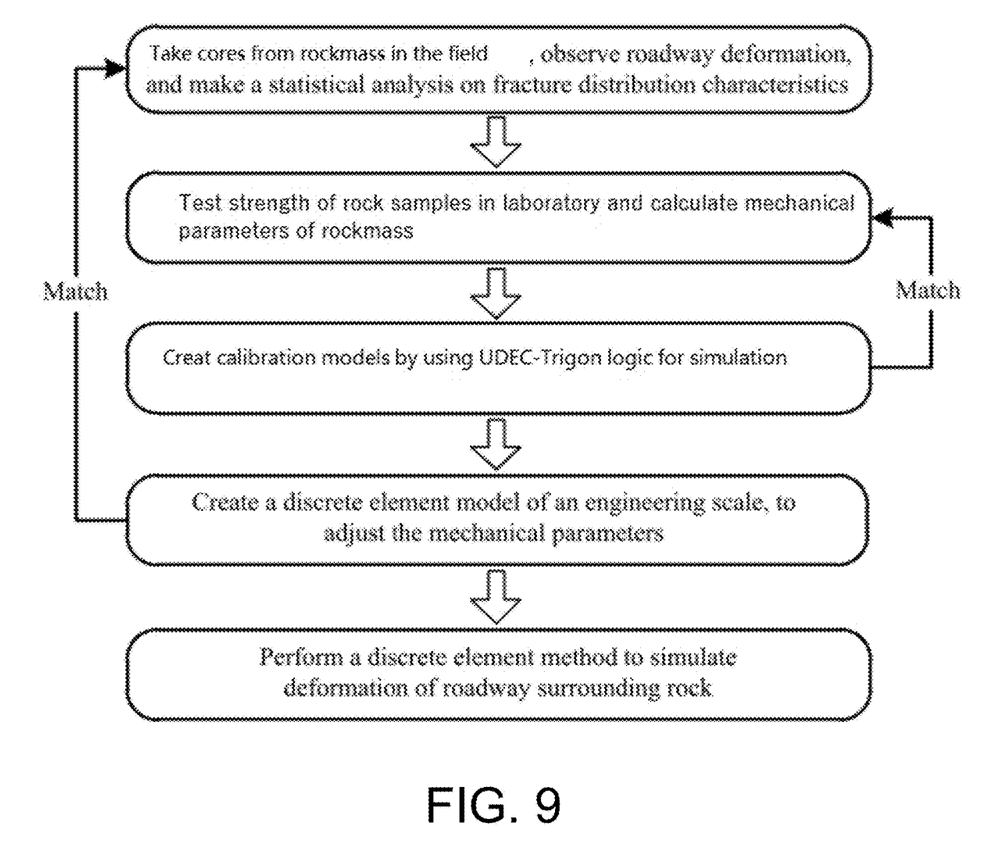
FIG. 9 is a flowchart of a discrete element method for modeling fracture evolution of roadway surrounding rock in the present invention.

By simulation with the UDEC Trigon model, fracture distribution in the coal pillar of 7 m in width after excavation of the air return roadway 15106 can be learned, as shown in FIG. 8. The coal pillar is divided into large-fracture zones and small-fracture zones according to the fracture distribution. It can be seen from FIG. 8 that, the large-fracture zones are on the two sides of the coal pillar. Tensile fractures develop to be almost broken within a distance of 2 m to the roadway and a distance of 3 m to the mined-out area, to form the large-fracture zones. Shear fractures develop within a distance range of 3 m to 4 m to the roadway, to form the small-fracture zones. The simulation results are highly consistent with field drilling observation results (FIG. 2*a*).

By verification with a field-scale large model, it indicates that field roadway deformation can be realistically simulated by putting Calibrated parameters into the UDEC Trigon model, and mine pressure behavior triggered by future excavation on the working face can be further predicted by use of the Calibrated parameters. Moreover, the method of the present invention is proved to be highly reliable and have a practical value.

What is claimed is:

1. A discrete element method for modelling a fracture evolution of a roadway surrounding rock, comprising following steps:
   S1: in a test roadway, observing deformation characteristics of the roadway and taking rock cores from coal seam and rock mass; recording deformation characteristics of the roadway surrounding rock, and monitoring distribution characteristics of fractures in roof and two ribs of the roadway; and taking rock cores from the roof and the coal seam, and recording RQD values of the roof rock cores and the coal seam rock cores;
   S2: separately making the obtained roof rock cores and the coal seam rock cores into standard intact rock, and carrying out experiments in mechanics to test an uniaxial compressive strength, a tensile strength, and an elastic modulus of the intact rock; and according to a functional relationship between a ratio of an elastic modulus of a rock mass to that of the intact rock and the RQD, and a functional relationship between an uniaxial compressive strength of the rock mass and that of the intact rock, determining the uniaxial compressive strength and the elastic modulus of the rock mass, wherein a tensile strength of the rock mass is 0.1 of its uniaxial compressive strength;
   S3: creating a calibration model by using a Trigon module in UDEC, wherein an average value of side lengths of triangular blocks in the calibration model is determined according to the distribution characteristics of fractures statistically analyzed in step S1; by using the uniaxial compressive strength, the tensile strength, and the elastic modulus of the rock mass calculated in step S2 as known characteristic values, performing an inversion with the calibration model to obtain parameters for a triangular block and parameters for a joint in the calibration model; and
   S4: creating a large-size numerical model with a field scale by using the UDEC, defining an area of study, and dividing the area of study into triangular blocks by using the Trigon module, wherein an average value of side lengths of the triangular blocks and the triangular block parameters are identical with those in the calibration model in step S3; forming rectangular blocks increasingly growing in length by division in areas outside the area of study; and based on the deformation characteristics of the roadway surrounding rock and the distribution characteristics of fractures that are observed in step S1, performing an inversion to obtain mechanical parameters of the rectangular blocks in the large-size numerical model.

2. The discrete element method for modelling the fracture evolution of the roadway surrounding rock according to claim 1, wherein the parameters for the triangular block and the parameters for the joint in the calibration model that are obtained by the inversion in step S3 respectively comprise a size and an elastic modulus of the triangular block, and a normal stiffness, a shear stiffness, a cohesion, a friction angle, and a tensile strength of the joint; and the inversion specifically comprises:
   a) separately creating a rectangular calibration model of 2 m in width and 4 m in height and a circular calibration model with a diameter of 2 m, wherein an average value of the side lengths of the triangular blocks is guaranteed to be consistent with a fracture length obtained based on field statistics;

b) setting the elastic modulus of the triangular blocks in the calibration model to be equal to that of the rock mass calculated according to a formula (II);

c) deducing normal stiffness $K_n$ of the joint between the triangular blocks according to a formula (IV), a ratio of a shear stiffness $K_s$ to the normal stiffness $K_n$ being 0.2; and determining a Poisson's ratio $\mu$ according to a variation in $K_s/K_n$, wherein the formula (IV) is specifically as follows:

$$K_n = n\left[\frac{K+(4/3)G}{\Delta Z_{min}}\right](1 \leq n \leq 10) \quad (IV)$$

wherein K and G are respectively a volume modulus and a shear modulus of the triangular blocks, in GPa, and are calculated according to equations $K=E/3(1-2\mu)$ and $G=E/2(1+\mu)$, $\mu$ being the Poisson's ratio of the block, and E being an elastic modulus of the block, in GPa; $\Delta Z_{min}$ is a minimum width of adjoining units in a vertical direction, in m; and n is equal to 10; and d) carrying out a series of uniaxial compression test and Brazilian splitting test by using the calibration model, to obtain stress-strain curves; employing means of trial and error iteration to make simulated mechanical parameters match the uniaxial compressive strength, the tensile strength, and the elastic modulus of the rock mass calculated in step S2; and finally performing an inversion to obtain a cohesion, an internal friction angle, and a tensile strength of the joint in the calibration model.

3. The discrete element method for modelling the fracture evolution of the roadway surrounding rock according to claim 2, wherein in step S1, a roadway surface displacement measuring station is mounted by means of a crisscross layout, the deformation characteristics of the roadway surrounding rock are recorded with an explosion-proof camera, the distribution characteristics of fractures in the roof and the two ribs of the roadway are monitored with a drilling observation instrument, and a distribution rule of lengths of fractures in a surface of a drill hole is quantified by means of drilling tracing.

4. The discrete element method for modelling the fracture evolution of the roadway surrounding rock according to claim 1, wherein in step S1, a roadway surface displacement measuring station is mounted by means of a crisscross layout, the deformation characteristics of the roadway surrounding rock are recorded with an explosion-proof camera, the distribution characteristics of fractures in the roof and the two ribs of the roadway are monitored with a drilling observation instrument, and a distribution rule of lengths of fractures in a surface of a drill hole is quantified by means of drilling tracing.

5. The discrete element method for modelling the fracture evolution of the roadway surrounding rock according to claim 4, wherein in step S1, the RQD values represents rock quality designation which is expressed by the following specific equation:

$$RQD = \frac{l}{L} \times 100\% \quad (I)$$

wherein l is a cumulative length of rock cores greater than or equal to 10 cm in length, in m; and L is a total length of the drill hole.

6. The discrete element method for modelling the fracture evolution of the roadway surrounding rock according to claim 4, characterized in that wherein in step S2, the functional relationship between the ratio of the elastic modulus of the rock mass to that of the intact rock and the RQD is expressed by the following specific equation:

$$E_m/E_r = 10^{0.0186 RQD - 1.91} \quad (II)$$

wherein $E_m$ is the elastic modulus of the rock mass, in GPa; and $E_r$ is the elastic modulus of the intact rock, in GPa.

7. The discrete element method for modelling the fracture evolution of the roadway surrounding rock according to claim 4, wherein in step S2, the functional relationship between the uniaxial compressive strength of the rock mass and that of the intact rock is expressed by the following specific equation:

$$\left(\frac{\sigma_{cm}}{\sigma_c}\right) = \left(\frac{E_m}{E_r}\right)^m \quad (III)$$

wherein $\sigma_{cm}$ and $\sigma_c$ are the uniaxial compressive strength of the rock mass and that of the intact rock respectively, in MPa; and m is equal to 0.63.

* * * * *